(12) United States Patent
Richter et al.

(10) Patent No.: US 6,250,443 B1
(45) Date of Patent: *Jun. 26, 2001

(54) DEVICE FOR WINDING AND UNWINDING LINES, AND APPARATUS EQUIPPED WITH SUCH A DEVICE

(75) Inventors: Helmut Richter, Baiersdorf; Peter Sypien, Uehlfeld, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/362,053

(22) Filed: Jul. 28, 1999

(30) Foreign Application Priority Data

Dec. 23, 1998 (DE) ......................................... 298 23 006 U (51) Int. Cl.⁷ ................................................... H02G 11/00
(52) U.S. Cl. ...................................................... 191/12.2 R
(58) Field of Search ............................ 191/12 R, 12.2 R, 191/12.2 A (56) References Cited

U.S. PATENT DOCUMENTS

| | | | |
|---|---|---|---|
| 4,565,333 | * | 1/1986 | Meneian .............................. 242/54 R |
| 5,145,390 | | 9/1992 | Kaul . |
| 5,332,171 | | 7/1994 | Steff . |
| 5,406,327 | * | 4/1995 | Guarnotta ........................... 191/12 R |
| 6,065,710 | * | 5/2000 | Richter et al. .................. 191/12.2 R |

FOREIGN PATENT DOCUMENTS

196 51 960   12/1998 (DE) .

* cited by examiner

Primary Examiner—S. Joseph Morano
Assistant Examiner—Robert J. McCarry, Jr.
(74) Attorney, Agent, or Firm—Schiff Hardin & Waite (57) ABSTRACT

A device for winding and unwinding lines has at least two rotatable drums onto which at least one line can be wound and from which at least one line can be unwound respectively, and a transmission connecting the drums such that one line is wound onto one drum when the other line is unwound from the other drum. An apparatus equipped with such a device allows one apparatus part to move relative to another apparatus part while winding/unwinding of the lines takes place.

16 Claims, 5 Drawing Sheets

DEVICE FOR WINDING AND UNWINDING LINES, AND APPARATUS EQUIPPED WITH SUCH A DEVICE

BACKGROUND OF THE INVENTION

1. Field of the Invention

The present invention is directed to a device for winding and unwinding at least two lines and an apparatus employing such a device, the lines connecting an apparatus part to electrically operated devices of the apparatus that can be dislocated relative to the apparatus part.

2. Description of the Prior Art

German PS 40 19 513 discloses a device with a rotatable drum arrangement for winding and unwinding a line. The drum arrangement has an outer, hollow-cylindrical drum that is rotatably seated around an inner hollow-cylindrical drum that is stationary relative to the outer drum. The outer drum accepts the line in the form of a ribbon cable and a rope. The ribbon cable and the rope can be wound and unwound in opposite directions on different regions of the outer drum. The device is arranged in an apparatus part of an apparatus that has a second apparatus part with electrically operated devices that can be adjusted relative to the first apparatus part. The ribbon cable electrically connects the two apparatus parts to one another, the ribbon cable and the rope respectively having ends secured to different ends of the second apparatus part. When a tensile force is exerted on the ribbon cable by moving the two apparatus parts relative to one another, the ribbon cable is unwound from the rotatable drum and the rope is wound on the rotatable drum and, given exertion of a tensile force on the rope due to opposite movement of the two apparatus parts relative to one another, the rope is unwound from the rotatable drum and the ribbon cable is wound onto the rotatable drum. A spring via which the rope end is secured to the second apparatus part serves the purpose of exerting a constant tensile force on the rope, and thus on the ribbon cable, so that this is wound onto the drum with a slight pre-stress.

The winding and unwinding of the ribbon cable, which, can have its other end connected to an energy supply and to a control and signal processing unit, onto the rotatable drum is possible only because a portion of the ribbon cable is wound in a helix around the inner drum. The respective surfaces of the two hollow-cylindrical drums have an opening through which the ribbon cable is conducted. The ribbon cable is initially conducted via a lateral opening of the inner drum through the opening of the surface of the inner drum in the region between the drums, is wound as a helix around the inner drum, and is conducted toward the exterior through the opening of the surface of the outer drum. The portion of the ribbon cable that is located between the drums has its section ends secured such to the inner and outer drum so that, given rotation of the outer drum around the inner drum, the ribbon cable is wound onto or is unwound from the surface of the outer drum and, when the ribbon cable is wound onto or unwound from the outer drum, the helix formed by the region of the ribbon cable lying between the drums is constricted or expands in the direction toward the surface of the inner drum.

The known device is only suitable for the acceptance of a ribbon cable that can be reliably wound onto or unwound from the outer drum, i.e. without forming loops. This is a disadvantage because ribbon cables are expensive and have a high space requirement when being wound onto a drum.

German PS 196 51 960 discloses an apparatus having a device for the transmission of electrical energy and/or of signals from one apparatus part to electrical devices that can be displaced relative to the apparatus part, using round lines. The device has a rotatable drum onto which another line is wound when one line is unwound.

A disadvantage of this known device is that the drum, which is composed of an outer and an inner, hollow-cylindrical drum with the outer drum rotating around the stationary inner drum, does not offer adequate space for the acceptance of the lines. Particularly the space between the outer and the inner drum wherein, as described above, the lines are wound in a helix around the inner drum, is not adequate for accepting lines having larger line diameters and given the condition of not having to implement the drums too large.

SUMMARY OF THE INVENTION

An object of the present invention is to provide a device of the type initially described wherein a dependable winding and unwinding of at least two lines onto the device is possible, and wherein the device exhibits adequate space for the acceptance of the lines. It is also an object of the invention to provide an apparatus of the type initially described wherein the transmission of energy and signals from the apparatus part to the electrically operated devices is free of malfunction.

According to the invention, the object directed to the device is achieved in a device having at least two rotatable drums onto each of which at least one line can be respectively wound and unwound, and a transmission connecting the drums such that one line is wound onto one drum when another line is unwound from the other drum. Preferably only one line is wound onto and unwound from each drum; in this way, the drums offer adequate space for the acceptance or intermediate storage of the lines. The transmission is preferably mechanical and makes it possible in a simple way for, when one line is unwound from one drum, with, for example, a tensile force exerted on the line, to wind the other line on the other drum. Ribbon cables as well as round cables can be wound and unwound with the device. Departing from the preferred embodiment of the device, however, the two drums can also be implemented such that more than one line can be wound onto or unwound from each of the drums. When, for example, it is provided that the device accepts three lines, then one line is wound onto and unwound from one drum and the two other lines are wound onto and unwound from different regions of the other drum. Due to the coupling at the two drums with the transmission, the winding of the one line ensues while the other two lines are unwound and vice versa. The two drums preferably have respective rotational axes which are different from one another, but proceeding substantially parallel to one another, and further drums for winding and unwinding further lines can be connected parallel to one or both of the drums, the further drums implementing the same rotational movements as the drums to which they are connected in parallel.

In one embodiment of the device a drive mechanism interacts with one of the drums or with the transmission. This is particularly advantageous when the lines are not to be tensilely stressed when being unwound.

According to one version of the invention, the drive mechanism has a drive element in the form of a belt, a chain or a toothed rack that interacts with a drive sheave in the form of a pulley, a chain wheel or a toothed rack sheave. The drive mechanism in a further version of the invention, however, can be an electrical drive, preferably an electric motor, so that the winding and unwinding of the lines can be motorized.

In a preferred embodiment of the invention each of the drums is formed by an outer hollow-cylindrical drum that is rotatable around an inner hollow-cylindrical drum which is stationary relative to the outer drum, and each line that can be wound onto or unwound from an outer drum is respectively conducted via an opening of the outer drum into the space between the outer and inner drum and is respectively wound helically around the inner drum in a guide helix loosely placed around the inner drum. Since the turn diameter and the number of turns of the lines in the space between the outer and inner drum, given winding and unwinding of the lines, change on the outer drums, the guide helix assures a uniform ply of lines in the space between the outer and inner drum in all cases. The guide helix can be loosely placed over the inner drum, so that adaptation to the number of turns of the lines is possible. When a number of lines are to be wound onto different regions of a drum and a number of lines are to be unwound from different regions of a drum, then a region accepting the helically wound line and having a guide helix is provided for each line in the space between the outer drum and the inner drum. The individual regions are made separate from one another.

The object relating to an apparatus is achieved in an apparatus having an inventive device with lines for the transmission of electrical energy and/or signals from one apparatus part to electrically operated devices which are displaceable relative to the apparatus part. By equipping the apparatus with the inventive device for winding and unwinding at least two lines, according to one version of the invention the lines for the transmission of energy and signals can be separate from one another. The separation of energy and signal lines minimizes disturbances due to crosstalk of energy to signal lines, and thus fewer disturbances occur during operation of the apparatus.

In a further version of the invention the apparatus has a second apparatus part fashioned as C-arm that is secured to the first apparatus part, which is fashioned as a holder of the C-arm and the C-arm is seated so as to be adjustable along its circumference at the holder. The two lines connect the holder and the C-arm to one another, with the lines being conducted enclosed inside the C-arm to an x-ray source and/or to an x-ray receiver that are arranged at the ends of the C-arm lying opposite one another. The covered (enclosed) guidance of the lines, for example in a cavity of the C-arm, protects the lines from damage. Preferably, at least one line is provided for the transmission of energy and at least one line is provided for the transmission of signals, and the C-arm can have lines running from one end to the other end that transmit energy and/or signals from one to the other end of the C-arm.

DESCRIPTION OF THE PREFERRED EMBODIMENTS

Figure 1:
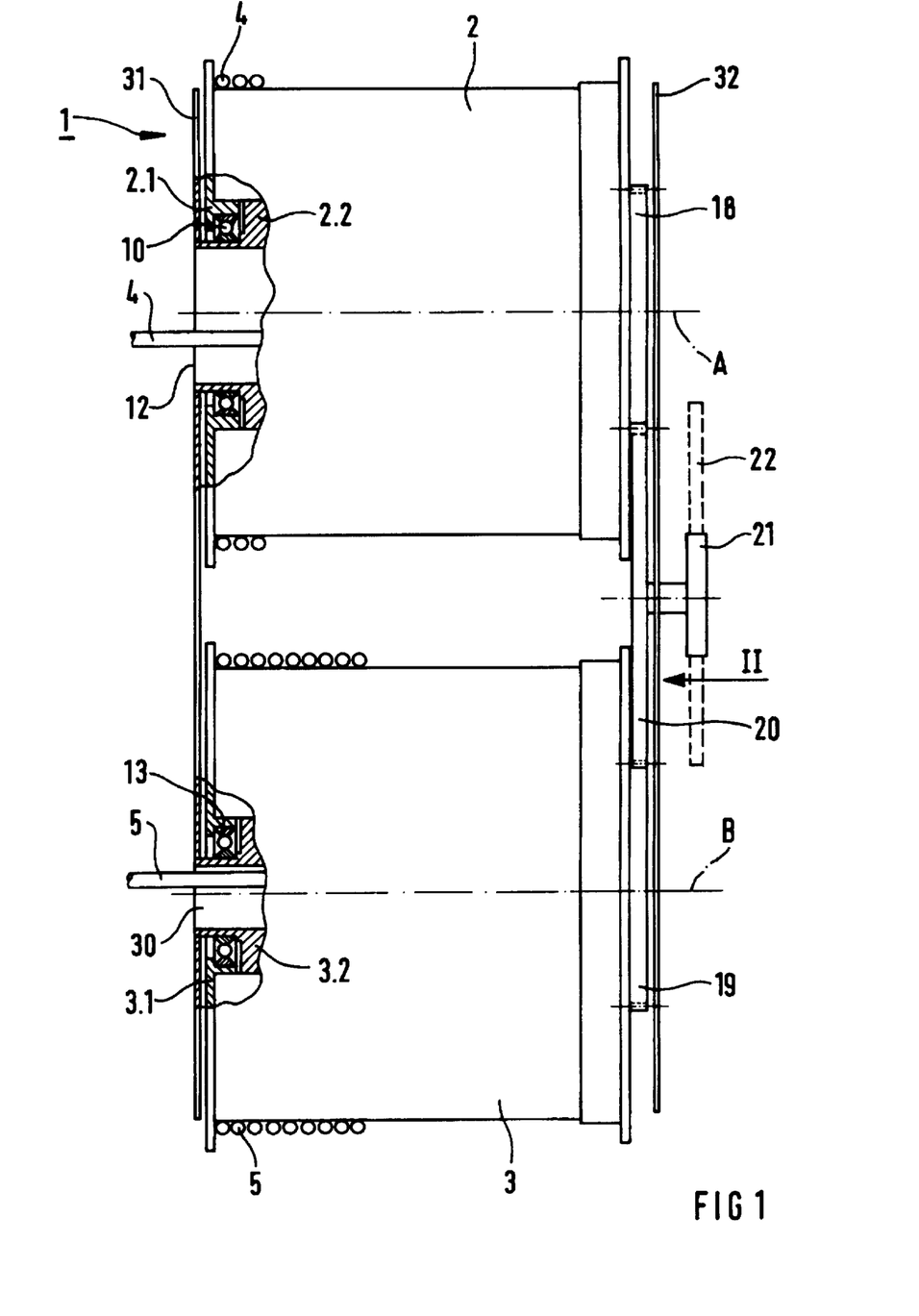
FIG. 1 is a front view, partly broken away and in section, of a device for winding and unwinding lines constructed in accordance with the principles of the present invention.

FIG. 1 shows an inventive device having two drums 2 and 3 respectively rotatable around axis A and axis B. In the embodiment, the drums 2 and 3 each serve for the acceptance of one line per drum. The lines are in the form of two round cables 4 and 5. The cables 4 and 5 are only schematically indicated in FIG. 1.

The drum 2 has an outer, hollow-cylindrical drum 2.1 that is rotatable around an inner hollow-cylindrical 2.2 that is stationary relative to the outer drum 2.1. The outer drum 2.1 is seated with ball bearings at each end relative to the inner drum 2.2 (only the ball bearing 10 being shown in the figures). The cable 4 can be wound onto the outer drum 2.1 and unwound from the outer drum 2.1 in a known way. The cable 4 is fixed in the region of an opening of the surface of the outer drum 2.1 that is not shown in FIG. 1, is conducted through this opening into the space between the outer and inner drum 2.1, 2.2, and is loosely helically wound around the inner drum 2.2 in a guide helix placed around the inner drum 2.2 in a way not shown in FIG. 1 (see the guide helix 26 in FIG. 4). The cable 4 is likewise fixed in the region of an opening of the surface of the inner drum 2.2 that is likewise not shown in FIG. 1 and is conducted toward the exterior through the opening of the inner drum 2.2 and a lateral opening 12 of the hollow-cylindrical, inner drum 2.2 Given unwinding events of the cable 4 from the outer drum 2.1, the cable helix becomes compressed (i.e., the spaces between successive turns decreases or becomes nonexistent) in a known way in the space between the outer and inner drum 2.1, 2.2, whereas the cable helix expands (i.e., the spaces widen) in a known way given winding events.

Figure 4:
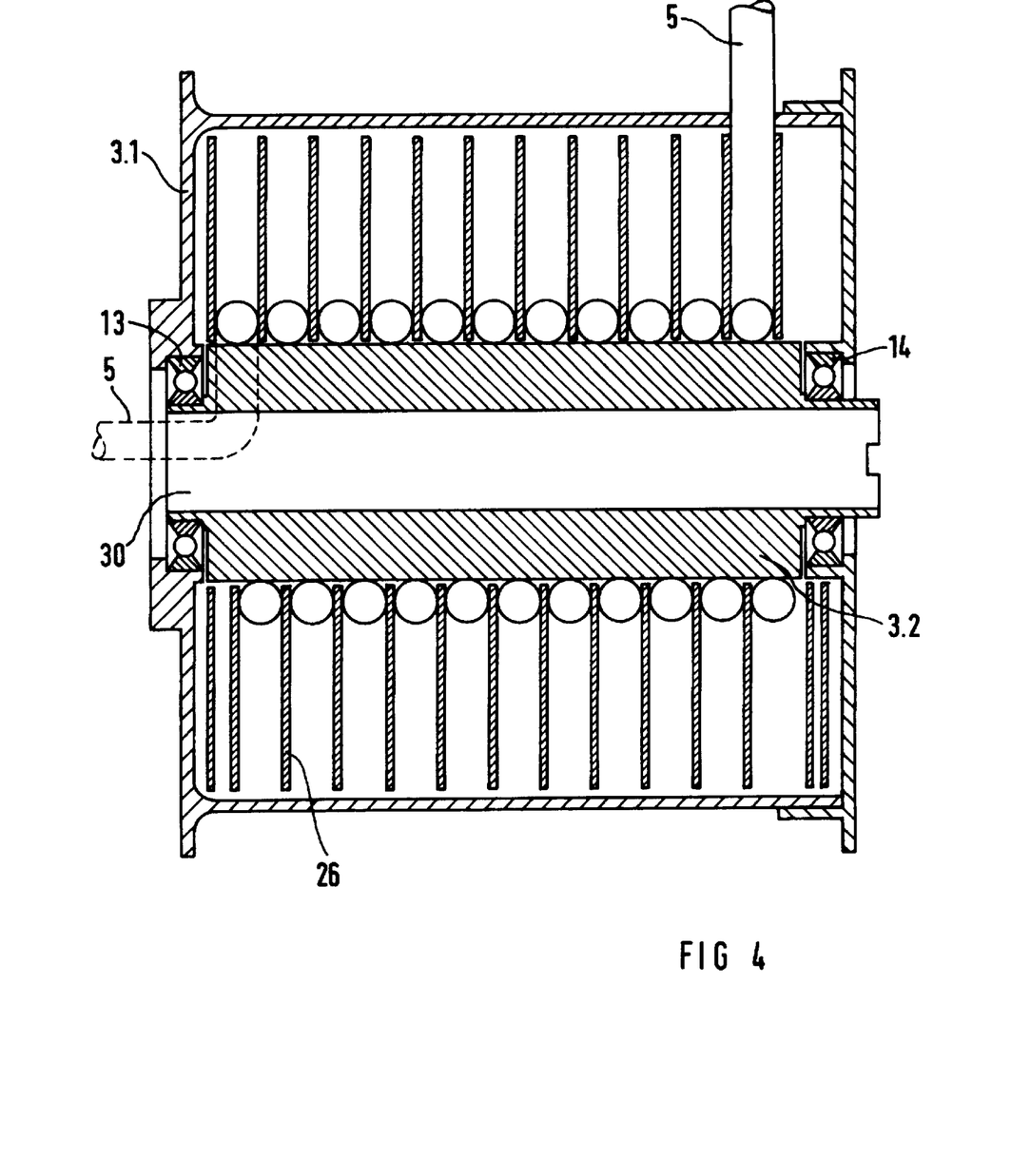
FIG. 4 is a sectional view of a drum in the device of FIG. 1.

The drum 3 is constructed in a way analogous to the drum 2 and has an outer drum 3.1 and an inner drum 3.2, the outer drum 3.1 being rotatably seated relative to the inner drum 3.2 with ball bearings at each end (only the ball bearing 13 being visible in FIG. 4). The drum 3 is provided for the acceptance of the cable 5. The cable guides for the cable 5 on and in the drum 3 essentially corresponds [sic] to the cable guide of the cable 4 on and in the drum 2.

In the exemplary embodiment, a mechanical transmission formed by gears is allocated to the drums 2 and 3, this connecting the two drums 2 and 3 to one another. The outer drum 2.1 is rigidly connected to a gear 18 that is rotatable around the axis A together with the outer drum 2.1. In an analogous way, the outer drum 3.1 is rigidly connected to a gear 19, so that the gear 19 is rotatable around the axis B together with the outer drum 3.1. The gear 18 interacts with a gear 20 and the gear 20 interacts with the gear 19 of the transmission (see FIG. 2), so that the outer drums 2.1 and 3.1 rotate in the same sense.

When unwinding, for example, the cable 4 from the outer drum 2.1 upon exertion of a tensile force on the cable 4, the outer drum 2.1 together with the gear 18 is placed in rotation around the axis A. Via the gear 20 and the gear 19 firmly connected to the outer drum 3.1, the outer drum 3.1 is thereby placed into rotation around the axis B in the same sense as the outer drum 2.1, and the cable 5 is wound onto the outer drum 3.1.

In order to avoid the exertion of tensile forces on the cables 4, 5 during unwinding events, which could damage the cables 4, 5 due to tensile stressing, the device 1 is provided with a drive mechanism as shown in FIG. 1, this interacting with the gear 20 of the transmission in the exemplary embodiment. The drive mechanism includes a pulley 21 firmly connected to the gear 20 and a belt 22 that is only schematically indicated in FIG. 1 and that is conducted around the pulley 21. Movement of the belt 22 via the pulley 21 effects a rotation of the pulley 21, and thus of the gear 20, which drives the outer drums 2.1 and 3.1 via the gears 18, 19. The winding and unwinding of the cables 4, 5 onto or from the outer drums 2.1 and 3.1, accordingly, is controllable via the belt drive, so that the cables 4, 5 are not tensilely stressed during unwinding.

Figure 2:
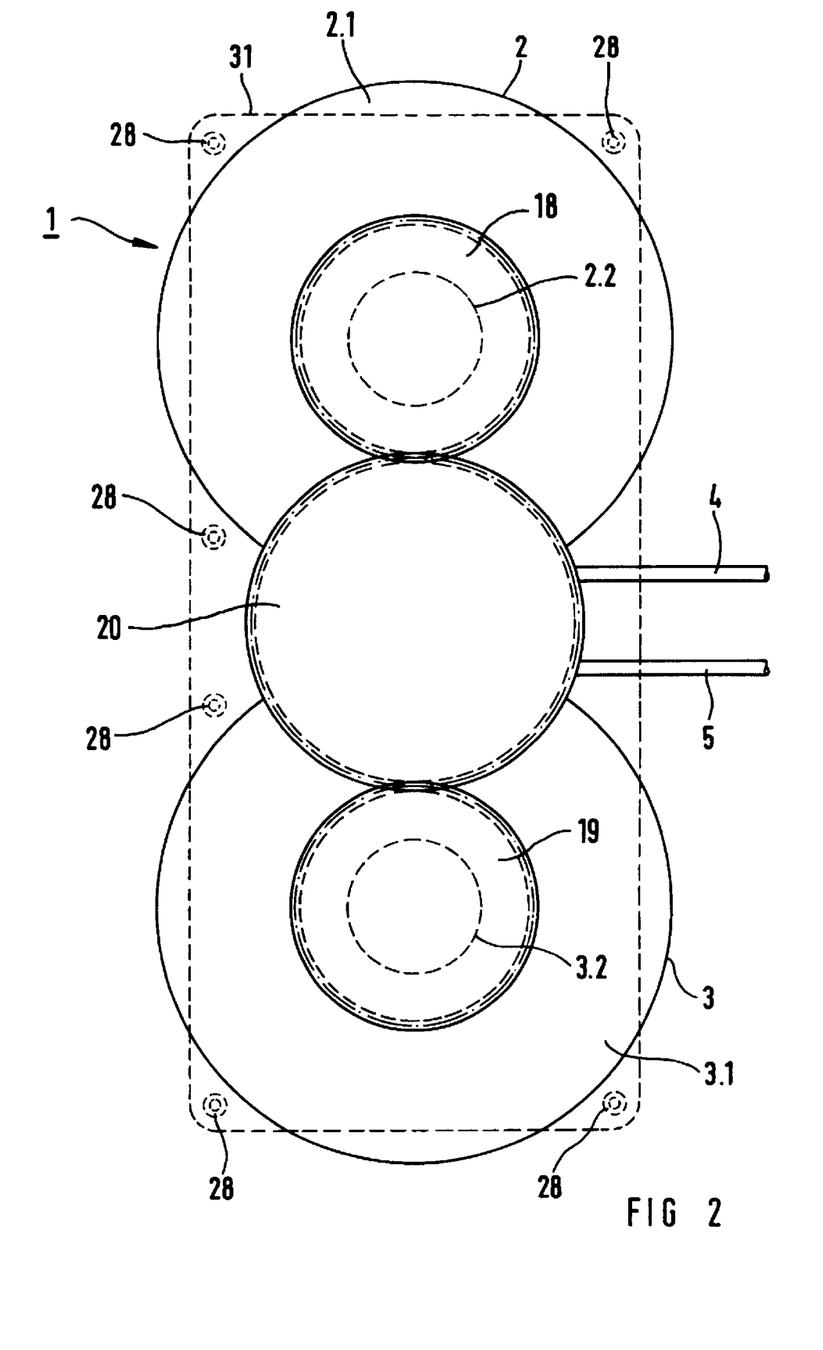
FIG. 2 is a view of the device shown in FIG. 1 as seen in the direction of the arrow II in FIG. 1.

The drums 2, 3, the transmission and at least a part of the device 1, moreover, are arranged between two fastening plates 31, 32 shown in FIG. 1 that are connected to one another with screws 28. FIG. 2 shows a view of the device 1 in the direction of the arrow II in FIG. 1 with the fastening plate 32 and drive mechanism removed. The fastening plate 31 is indicated with broken lines in FIG. 2.

Figure 3:
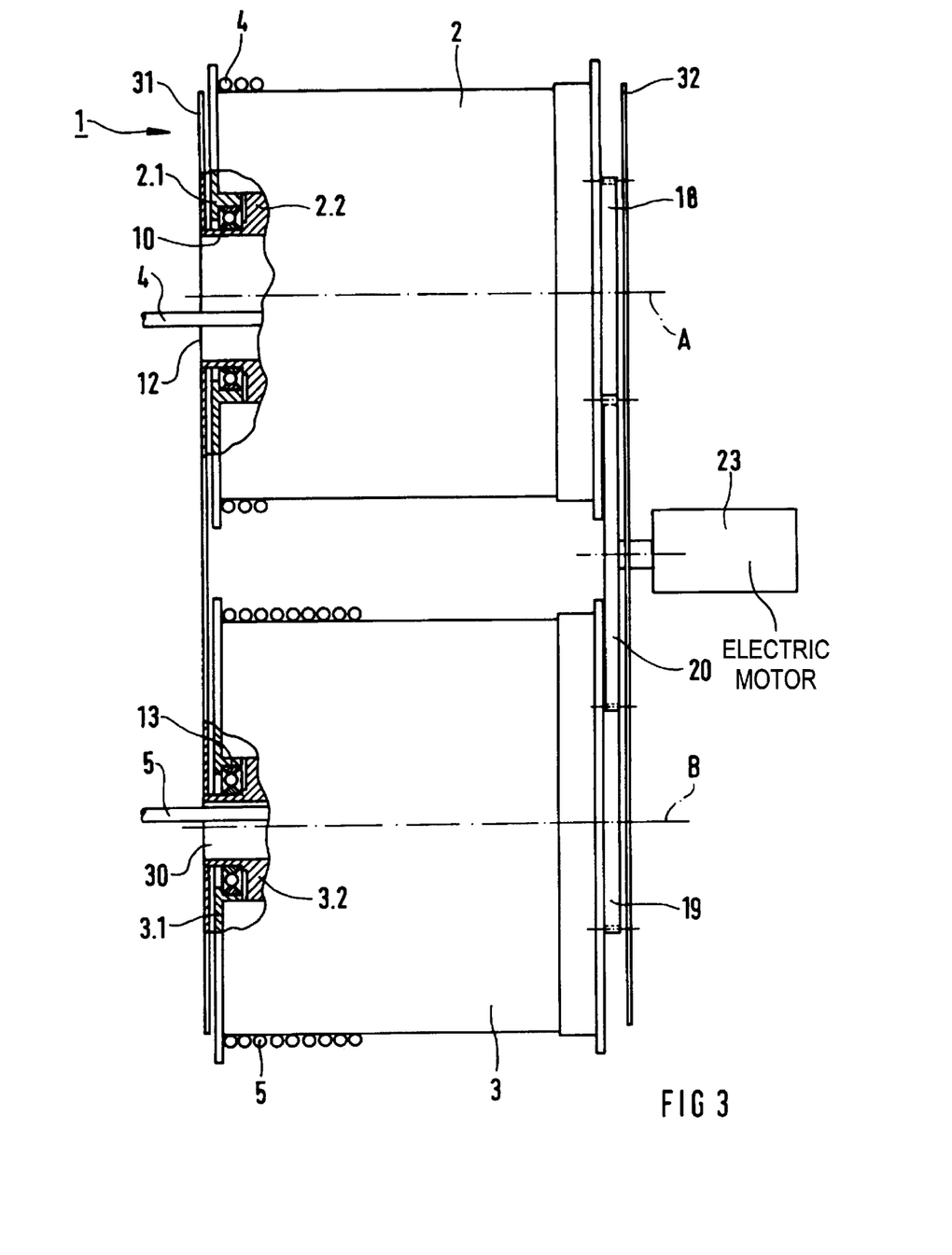
FIG. 3 is a front view, partly broken away and partly in section, of a further embodiment of a device for winding and unwinding lines constructed in accordance with the principles of the present invention.

FIG. 3 shows a further embodiment of the inventive device 1, wherein a drive in the form of an electric motor 23 is provided instead of the pulley 21 and the belt 22. The electric motor 23 interacts with the gear 20 such that, dependent on the drive direction of the electric motor 20, the drums 2, 3 are driven via the gears 18, 19 to wind and unwind the cables 4, 5. In this way, the unwinding as well as the winding of the cables 4, 5 can ensue in motorized fashion.

The electric motor 23 need not directly interact with the gear 20, but alternatively can directly interact with one of the gears 18, 19 of the gearing or with one of the two drums 2, 3. The same is also true of the pulley 21 and the belt 22.

FIG. 4 shows the functioning of the aforementioned guide helices with reference to the drum 3. In the exemplary embodiment, each of the drums 2, 3 is provided with its own guide helix. The cable 5 of the drum 3 is guided in a guide helix 26, with the guide helix 26 separating the individual turns of the cable 5 wound helically around the inner drum 3.2 from one another. FIG. 4 shows that case wherein the cable 5 is entirely unwound from the outer drum 3.1, whereby the cable helix is comprised in regions between the outer and inner drum 3.1, 3.2. When cable 5 is wound onto the outer drum 3.1, the cable helix widens in the regions between the outer and inner drum 3.1, 3.2. In both instances, which differ on the basis of the number of turns and the diameters of the turns of the cable helices, the guide helix assures a uniform ply (layering) of the cable 5. The cable 4 is guided with a guide helix (not shown in the figures) in the region between the outer drum and the inner drum 2.1, 2.2 in a way analogous to the cable 5.

The transmission of the device 1 need not be constructed such that the drums 2 and 3 move in the same direction as one another. The transmission alternatively can be implemented such that the drums 2 and 3 rotate oppositely relative to one another, in which case the cable guide of the cables 4, 5 is correspondingly adapted in order to enable winding of one cable when the other cable is unwound.

The transmission need not be composed of gears but alternatively can be a chain or belt drive.

Instead of the pulley 21 and the belt 22, the device from FIG. 1 can also be provided with a chain interacting with a chain wheel or with a toothed rack interacting with the gear as a drive mechanism.

Moreover, the drive in FIG. 3 may be of a different type from the described electric motor 23.

The two drums 2, 3 need not exhibit the same diameter as in the case of the exemplary embodiment. The diameters of the drums 2, 3 can differ from one another dependent on the maximally permitted bending of a cable to be wound onto one of the drums 2, 3. The transmission is appropriately designed so that the same length of cable wound on the drum 2 and on the drum 3 is wound or becomes free given winding and unwinding events.

Figure 5:
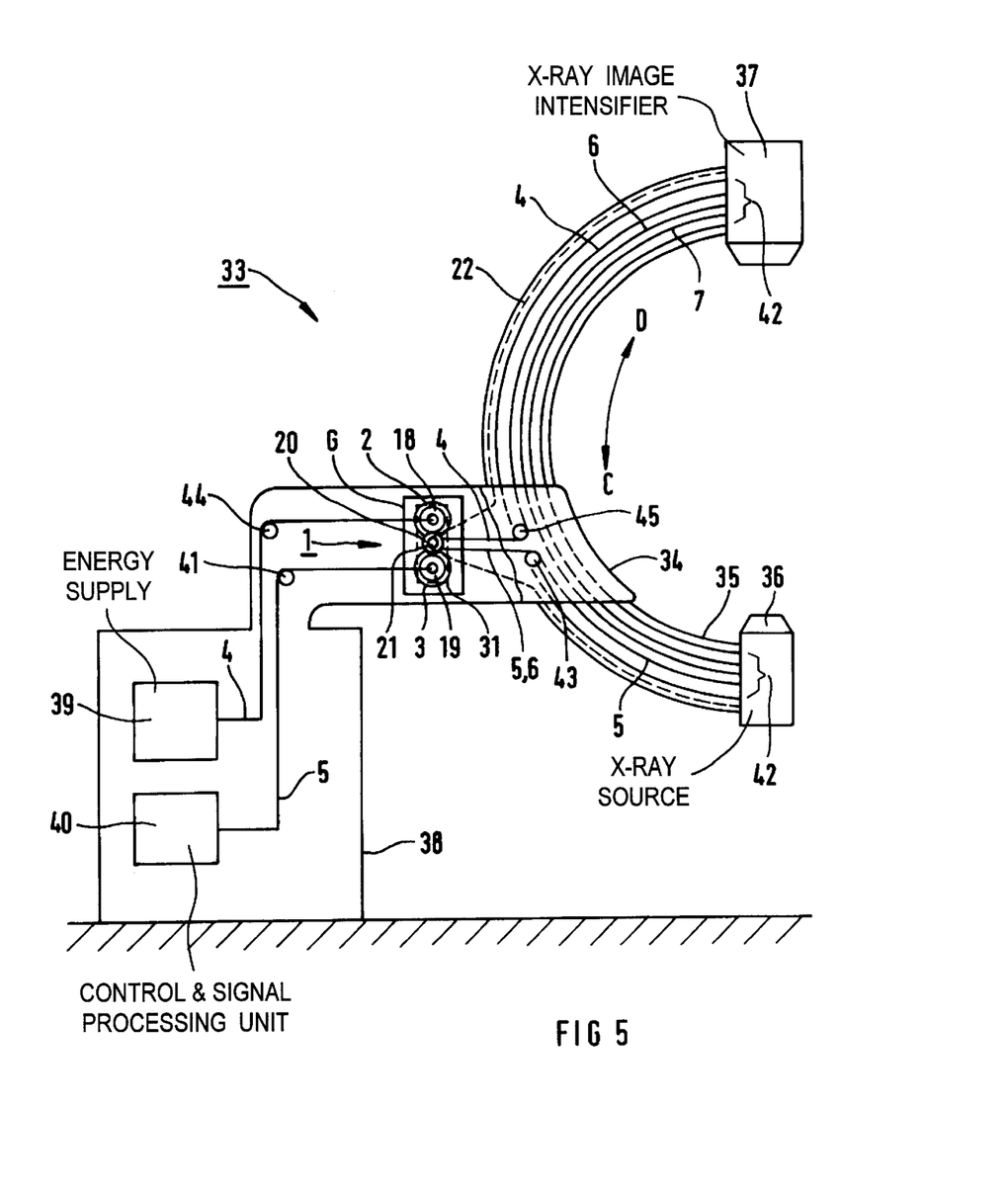
FIG. 5 is a schematic block diagram of an apparatus, in the form of a C-arm x-ray apparatus, equipped with a device for winding and unwinding lines in accordance with the invention.

FIG. 5 shows an embodiment of an inventive apparatus with the device 1 shown in FIG. 1 arranged in a housing G. The device 1 is only schematically indicated in FIG. 5 with its drums 2, 3, the transmission, the drive mechanism and the fastening plate 31. In the exemplary embodiment, the apparatus is a C-arm x-ray apparatus 33. The lines of the device 1, as in the above-described exemplary embodiment of the device 1, are in the form of round electrical cables that are provided for the transmission of electrical energy and signals respectively.

The C-arm x-ray apparatus 33 has a first apparatus part fashioned as holder 34 and a second apparatus part fashioned as C-arm 35. The C-arm 35 is adjustably held along its circumference by the holder 34. At its ends, the C-arm 35 carries an x-ray source 36 and an x-ray image intensifier 37 lying opposite one another. The holder 34 is secured to a further apparatus part 38 of the C-arm x-ray apparatus 33 that contains an energy supply 39 and a control and signal processing unit 40 for the operation of the x-ray source 36 and of the x-ray image intensifier 37. The control and signal processing unit 40 makes control signals available operating the x-ray source 36 and the x-ray image intensifier 37 and is also provided for processing image signals acquired with the x-ray image intensifier 37.

The aforementioned and above-described device 1 is accepted in the holder 34. The cables 4, 5 of the device 1 connect the C-arm 35, the holder 34 and the apparatus part 38 to one another.

The cable 5 proceeds from the control and signal processing unit 40 via a deflection roller 41 to the device 1. The cable 5 is guided via the lateral opening 30 of the inner drum 3.2 (see FIG. 1) into the drum 3 in the above-described way, is helically wound in the guide helix 26 around the inner drum 3.2 and is wound through the opening of the drum 3.1 (see FIG. 4) onto the outer drum 3.1. From the drum 3, the cable 5 is conducted via a deflection roller 43 to a shaft 42 of the C-arm 35 in which it is conducted to the x-ray source 36 and secured to the C-arm 35 in the region of the x-ray source 36.

In a way analogous to the cable 5, the cable 4 is conducted from the energy supply 39 via a deflection roller 44 to the device 1. The cable 4 is conducted via the lateral opening 12 of the inner drum 2.1 and the opening of the inner drum 2.1 into the region between the inner and outer drums 2.2, 2.1, is helically wound around the inner drum 2.2 in the guide helix (not shown in the figure), is conducted through the opening of the outer drum 2.1 and wound onto the outer drum 2.1. From the outer drum 2.1, the cable 4 is conducted via a deflection roller 45 to the shaft 42 of the C-arm 35 in which it is conducted to the x-ray image intensifier 37 and secured to the C-arm 35 in the region of the x-ray image intensifier 37.

In the exemplary embodiment, the cable 5 is provided for the transmission of control signals from the control and signal processing unit 40 to the x-ray source 36. Via the cable 5, control signals are thereby also transmitted that are provided for the x-ray image intensifier 37 and are supplied via a cable 6 proceeding in the shaft 42 from the x-ray source 36 to the x-ray image intensifier 37. The cables 5, 6 thereby serve as well for the transmission of image signals acquired with the x-ray image intensifier 37 to the control and signal processing unit 40. The cable 4 serves for the transmission of energy from the energy supply 38 that is provided for the x-ray source 36 and for the x-ray image intensifier 37. A cable 7 that is conducted in the shaft 42 from the x-ray image intensifier 37 to the x-ray source 36 transmits the energy provided via the cable 4, together with the energy for the x-ray image intensifier 37, to the x-ray source 36. A separation of energy and signal lines thus ensues with the cables 4 through 7 in order to avoid disturbing influences during operation of the C-arm x-ray apparatus 33 caused by crosstalk between energy and signal lines.

In the exemplary embodiment, the C-arm 35 is also provided with the belt 22 that, as schematically indicated, proceeds covered along the circumference of the C-arm 35, and interacts with the pulley 21 coupled to the transmission of the device 1 for the drive of the outer drums 2.1, 3.1.

When the C-arm 35 is moved in a direction C in the holder 34, then the belt 22 effects a rotation of the pulley 21 which interacts in the above-described way with the transmission such that the cable 4 is wound onto the outer drum 2.1, and the cable 5 is simultaneously unwound from the outer drum 3.1. When the C-arm 35 is subsequently moved in a direction D, then the belt 22 effects a reverse rotation of the pulley 21, so that the drums 2, 3 are driven via the transmission so that the cable 4 is unwound from the outer drum 2.1 and the cable 5 is wound onto the outer drum 3.1.

The holder 34, moreover, need not be rigidly connected to the apparatus part 38. The holder 34 can be seated so as to be height-adjustable and pivotable relative to the apparatus part 38. In this case, however, at least one further must be provided in the apparatus part 38 that correspondingly follows the cables 4, 5 for the purpose of the height adjustment and pivoting of the holder 34.

In the C-arm x-ray apparatus 33, the device 1 need not be provided at the holder 34 but, in a correspondingly modified embodiment of the inventive apparatus, can be allocated to the C-arm 35.

Instead of the device 1 from FIG. 1, the C-arm x-ray apparatus 33 can be provided with the device 1 according to FIG. 3.

The apparatus equipped with the inventive device 1 need not be a C-arm x-ray apparatus 33, but can be a some other type of apparatus.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for winding and unwinding lines, comprising:
    a first line;
    a second line;
    a first rotatable drum onto which said first line is wound and from which said first line is unwound;
    a second rotatable drum onto which said second line is wound and from which said second line is unwound; and
    a transmission connected to each of said first drum and said second drum for rotating said drums so that said first line is wound onto said first drum when said second line is unwound from said second drum and so that said first line is unwound from said first drum when said second line is wound onto said second drum.

2. A device as claimed in claim 1 further comprising a drive mechanism connected to said first drum for rotating said first drum and, via said transmission, rotating said second drum.

3. A device as claimed in claim 2 wherein said drive mechanism comprises a drive sheave and a drive element mechanically connecting said drive sheave and said first drum, said drive element being selected from the group of drive elements consisting of a belt, a chain, and a toothed rack.

4. A device as claimed in claim 2 wherein said drive mechanism comprises an electrical motor.

5. A device as claimed in claim 1 further comprising a drive mechanism connected to said second drum for rotating said second drum and, via said transmission, rotating said first drum.

6. A device as claimed in claim 5 wherein said drive mechanism comprises a drive sheave and a drive element mechanically connecting said drive sheave and said second drum, said drive element being selected from the group of drive elements consisting of a belt, a chain, and a toothed rack.

7. A device as claimed in claim 5 wherein said drive mechanism comprises an electrical motor.

8. A device as claimed in claim 1 further comprising a drive mechanism connected to said transmission for rotating each of said first drum and said second drum.

9. A device as claimed in claim 8 wherein said drive mechanism comprises a drive sheave and a drive element mechanically connecting said drive sheave and said transmission, said drive element being selected from the group of drive elements consisting of a belt, a chain, and a toothed rack.

10. A device as claimed in claim 8 wherein said drive mechanism comprises an electrical motor.

11. A device as claimed in claim 1 wherein said first drum comprises:
    an inner, hollow-cylindrical drum;
    an outer, hollow-cylindrical drum that is rotatable around said inner, hollow-cylindrical drum, said inner, hollow-cylindrical drum being stationary relative to said outer, hollow-cylindrical drum;
    said outer, hollow-cylindrical drum having an opening therein and said outer, hollow-cylindrical drum and said inner, hollow-cylindrical drum having a space therebetween;
    a guide helix loosely disposed around said inner, hollow-cylindrical drum; and
    said first line being wound around said outer, hollow-cylindrical drum and being conductive through said opening and being wound around said inner, hollow-cylindrical drum in said guide helix in said space.

12. A device as claimed in claim 1 wherein said second drum comprises:
    an inner, hollow-cylindrical drum;
    an outer, hollow-cylindrical drum that is rotatable around said inner, hollow-cylindrical drum, said inner, hollow-cylindrical drum being stationary relative to said outer, hollow-cylindrical drum;
    said outer, hollow-cylindrical drum having an opening therein and said outer, hollow-cylindrical drum and said inner, hollow-cylindrical drum having a space therebetween;
    a guide helix loosely disposed around said inner, hollow-cylindrical drum; and
    said second line being wound around said outer, hollow-cylindrical drum and being conductive through said opening and being wound around said inner, hollow-cylindrical drum in said guide helix in said space.

13. An apparatus comprising:
- a first electrically operated device and a second electrically operated device;
- a first electric line connected to said first electrically operated device for conducting electric signals thereto;
- a second electric line, separate from said first electric line, connected to said second electrically operated device for supplying energy thereto;
- a stationary apparatus part to which said electrically operated devices are displaceably mounted; and
- a device for winding and unwinding said first electric line and said second electric line as said electrically operated devices are displaced relative to said apparatus part, said device for winding and unwinding comprising a first drum, a second drum, and a transmission connecting said first drum and said second drum so that said first electric line is wound onto said first drum as said second electric line is unwound from said second drum and so that said first electric line is unwound from said first drum as said second electric line is wound onto said second drum.

14. An apparatus as claimed in claim 13 further comprising a third electric line and a fourth electric line respectively connected to said first and said second electrically operated devices wherein said first and second electrically operated devices require or produce signals during operation thereof and which consume energy, and wherein said first and said third electric lines conduct said signals, and said second and said fourth electric lines conduct said energy.

15. An apparatus as claimed in claim 13 wherein said apparatus part is a first apparatus part, and said apparatus further comprising a second apparatus part, on which said first and second electrically operated devices are mounted, said first electric line and said second electric line proceeding between said first apparatus part and said second apparatus part.

16. An apparatus as claimed in claim 14 wherein said second apparatus part comprises a C-arm and wherein said first apparatus part comprises a holder for said C-arm, and wherein said first electrically operated device comprises an x-ray source mounted at one end of said C-arm, and said second electrically operated device comprises an x-ray receiver mounted at an opposite end of said C-arm from said x-ray source, said C-arm having a circumference and being movable in said holder along said circumference.

* * * * *